(12) United States Patent
Padia et al.

(10) Patent No.: US 9,067,902 B2
(45) Date of Patent: Jun. 30, 2015

(54) EPOXIDATION PROCESS WITH POST-CONDITIONING STEP

(71) Applicant: Scientific Design Company, Inc., Little Ferry, NJ (US)

(72) Inventors: Ashok S. Padia, Glen Rock, NJ (US); Hassan Eisa Al-Ahmadi, Washington Township, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 14/152,519

(22) Filed: Jan. 10, 2014

(65) Prior Publication Data

US 2014/0200357 A1 Jul. 17, 2014

Related U.S. Application Data

(60) Provisional application No. 61/751,465, filed on Jan. 11, 2013.

(51) Int. Cl.
| | |
|---|---|
| *C07D 301/03* | (2006.01) |
| *C07C 43/00* | (2006.01) |
| *C07C 29/00* | (2006.01) |
| *C07D 301/10* | (2006.01) |
| *C07D 301/08* | (2006.01) |
| *C07C 29/10* | (2006.01) |

(52) U.S. Cl.
CPC ............ *C07D 301/10* (2013.01); *C07D 301/08* (2013.01); *C07C 29/106* (2013.01)

(58) Field of Classification Search
CPC .. C07C 29/106; C07C 31/202; C07D 301/10; C07D 301/08
USPC .................................. 549/536; 568/680, 867
See application file for complete search history.

(56) References Cited

U.S. PATENT DOCUMENTS

| | | | |
|---|---|---|---|
| 3,563,914 A | 2/1971 | Wattimena | |
| 3,702,259 A | 11/1972 | Nielsen | |
| 4,761,394 A | 8/1988 | Lauritzen | |
| 4,766,105 A | 8/1988 | Lauritzen | |
| 4,874,879 A | 10/1989 | Lauritzen et al. | |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,155,242 A | 10/1992 | Shankar et al. | |
| 5,187,140 A | 2/1993 | Thorsteinson et al. | |
| 5,407,888 A | 4/1995 | Herzog et al. | |
| 7,102,022 B2 | 9/2006 | Evans et al. | |
| 8,536,353 B2 * | 9/2013 | Matusz | ......................... 549/536 |
| 2004/0110971 A1 | 6/2004 | Evans et al. | |
| 2007/0037991 A1 | 2/2007 | Rizkalla | |

(Continued)

OTHER PUBLICATIONS

International Search Report dated May 15, 2014, received in a corresponding foreign application.

*Primary Examiner* — T. Victor Oh
(74) *Attorney, Agent, or Firm* — Scully, Scott, Murphy & Presser, P.C.

(57) ABSTRACT

A method for the epoxidation of an olefin comprising the steps of reacting a feed gas composition containing an olefin, oxygen, and a moderator having a post-conditioning step where the catalyst is exposed to reactor feed having a chlorides concentration of from about 5 ppm to about 7 ppm and at a temperature of about 215° C. to about 225° C.

10 Claims, 3 Drawing Sheets

(56) References Cited

U.S. PATENT DOCUMENTS

| | | |
|---|---|---|
| 2009/0028339 A1 | 1/2009 | Goodman et al. |
| 2011/0015548 A1 | 1/2011 | Aldrich et al. |
| 2011/0015549 A1 | 1/2011 | Eckhouse et al. |
| 2011/0152551 A1 | 6/2011 | Sachs et al. |

* cited by examiner

EPOXIDATION PROCESS WITH POST-CONDITIONING STEP

CROSS REFERENCE TO RELATED APPLICATION

The present invention claims the benefit of U.S. Provisional Patent Application No. 61/751,465 filed Jan. 11, 2013, the entire content and disclosure of which is incorporated herein by reference.

FIELD OF THE INVENTION

The present invention relates to a method for the epoxidation of an olefin in the presence of an added moderator.

BACKGROUND OF THE INVENTION

Though present in natural settings at minute quantities, ethylene oxide was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist Theodore Lefort. Lefort used a solid silver catalyst with a gas phase feed that included ethylene and utilized air as a source of oxygen.

In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. Worldwide production in the year 2010 was about 22 million tons. About seventy percent of the ethylene oxide produced is further processed into ethylene glycol; about twenty percent of manufactured ethylene oxide is converted to other ethylene oxide derivatives and only a relatively small amount of ethylene oxide is used directly in applications such as vapor sterilization.

The growth in the production of ethylene oxide has been accompanied by continued intensive research on ethylene oxide catalysis and processing, which remains a subject of fascination for researchers in both industry and academia. Of particular interest in recent years has been the proper operating and processing parameters for the production of ethylene oxide using so-called "high selectivity catalysts", that is Ag-based epoxidation catalysts that contain small amounts of "promoting" elements such as rhenium and cesium.

With respect to these Re-containing catalysts, there has been considerable interest in determining the optimum conditioning or start-up conditions, since Re-containing catalysts require a conditioning period to maximize selectivity. Without this conditioning or "initiation" procedure, Re-containing, high-selectivity catalysts will not exhibit higher selectivity, but will perform like conventional "high activity" catalysts.

These conditioning procedures are often directed to ensuring the catalyst has a performance-enhancing amount of chloride. The presence of chloride plays a key role in maintaining the catalyst's selectivity—the efficiency of the partial oxidation of ethylene to ethylene oxide. This is especially the case with respect to rhenium-containing, high selectivity catalysts, which are very dependent on the presence of chlorides to achieve optimal performance. Examples of such procedures were previously disclosed in U.S. Pat. No. 4,874,879 to Lauritzen et al. and U.S. Pat. No. 5,155,242 to Shanker et al., which disclose start-up processes in which a Re-containing catalyst is pre-chlorinated prior to the introduction of oxygen into the feed and the catalyst is allowed to "pre-soak" in the presence of chloride at a temperature below that of the operating temperature. While some improvement in overall catalyst performance has been reported using these prior art methods, the pre-soaking and conditioning nonetheless impose a substantial delay before normal ethylene oxide production can begin after oxygen is added into the feed. This delay in production may either partially or entirely negate the benefit of increased selectivity performance of the catalyst.

Temperature is also an important aspect of conditioning—as shown, for example, in the proposed start-up process disclosed in U.S. Pat. No. 7,102,022 to Evans et al., which discloses contacting a Re-containing catalyst bed with a feed comprising oxygen and holding the temperature of the catalyst bed above 260° C. for a period of time of up to 150 hours. Again, while some improvement in catalyst performance may be obtained by this prior art method, there are also inherent disadvantages to this process, notably the high temperatures required during start-up.

Thus, the treatment methods for activating a Re-containing epoxidation catalyst disclosed in the aforementioned prior publications may provide some improvement in catalyst performance, but also have a number of deficiencies. However, given the improvement that an optimized activation process can impart to the selectivity of a Re-containing epoxidation catalyst, the full range of activation processes have not been fully explored. For these reasons there is a continuing need in the art for an improved conditioning procedure for use in olefin epoxidation.

BRIEF SUMMARY OF THE INVENTION

The present invention relates to a method for the epoxidation of an olefin comprising: initiating an epoxidation reaction by reacting a feed gas composition containing ethylene, oxygen, and a chloride moderator present at a concentration of from about 0.5 ppm to about 3 ppm, in the presence of an epoxidation catalyst at a temperature of about 245° C. to about 265° C.; increasing the moderator concentration to about 5 ppm to about 7 ppm and lowering the temperature to about 215° C. to about 225° C.; and maintaining the moderator concentration within the range of 5 ppm to about 7 ppm and the temperature in the range of about 215° C. to about 225° C. for a time period of about 50 hours to about 150 hours.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

All parts, percentages and ratios used herein are expressed by volume unless otherwise specified. All documents cited herein are incorporated by reference.

It has been discovered in the present invention that for many operators and in many ethylene oxide plants, that the conditioning of a catalyst can be significantly improved by adding an additional "post-conditioning" step in which the chloride concentration is significantly increased at relatively low temperatures. While this causes a temporary reduction in selectivity performance (visible as a "trench" in a graph of selectivity versus time—see FIG. 1) this high chloride conditioning process results in catalyst performance of both superior selectivity and superior stability.

The present invention is directed to the gas phase epoxidation of an olefin to form an olefin oxide by contacting a Re-containing silver-based catalyst in a reactor with a feed that contains at least oxygen, an olefin, and chlorides. It has been discovered in the present invention that improved catalyst performance over the useful life of the catalyst can be obtained by adding a post-conditioning step after a conventional conditioning step. In this post-conditioning step, the catalyst is exposed to a reactor feed having a very high chloride concentration, such as greater than 5 ppm, but at low temperatures (such as between 215° C.-225° C.). This technique of using high chlorides is contrary to conventional practice as in typical plant practice operators wish to avoid these high chloride concentrations because such "overchloriding" reduces the selectivity of the catalyst (and indeed a temporary reduction in selectivity is observed in the process practiced according to the present invention). However, after the completion of the post-conditioning step and after the chloride concentration is reduced to normal operating levels, the selectivity is quickly recovered and returns to normal operating levels. And by using this post-conditioning step, important technical effects are achieved—viz., improved instantaneous selectivity, average selectivity and catalyst stability.

Although not wishing to be limited by theory an explanation can be provided for how these technical effects are achieved. This explanation begins with the observation that even when instrument measurements indicate high levels of chloride in the reactor feed mixture this does not necessarily mean that a performance-enhancing amount of chloride is actually present on the catalyst surface. Rather, the measured amount of chloride can be misleading for a number of reasons, such as, for example: the dynamics of the gas-solid interface that may have prevented the accumulation of chloride on the catalyst surface (especially at higher temperatures), while in addition stripping by certain hydrocarbons may greatly reduce the presence of chloride compounds already on the catalyst surface.

Accordingly, it is believed, without being limited by theory, that adding a post-conditioning step addresses these problems. In the post-conditioning step, the reactor feed mixture contains high concentrations of chloride to increase the amount of chloride available for adsorption at the catalyst surface. Meanwhile, the relatively low post-conditioning temperature range of 215° C.-225° C. shifts the chloride adsorption-desorption equilibrium to favor chloride accumulation so that more of the available chloride is adsorbed.

The process of the present invention will be described in greater detail after a brief discussion of the silver catalyst to be used in the process.

Silver-Based Epoxidation Catalyst

The silver-based epoxidation catalyst includes a support, and at least a catalytically effective amount of silver or a silver-containing compound; also present is a promoting amount of rhenium or a rhenium-containing compound; also optionally present is a promoting amount of one or more alkali metals or alkali-metal-containing compounds. The support employed in this invention may be selected from a large number of solid, refractory supports that may be porous and may provide the preferred pore structure. Alumina is well known to be useful as a catalyst support for the epoxidation of an olefin and is the preferred support. The support may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. The support may comprise at least about 95 wt. % alpha-alumina; preferably, at least about 98 wt. % alpha-alumina. The remaining components may include inorganic oxides other than alpha-alumina, such as silica, alkali metal oxides (e.g., sodium oxide) and trace amounts of other metal-containing or non-metal-containing additives or impurities.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. Equivalent diameter is the diameter of a sphere having the same external surface (i.e., neglecting surface within the pores of the particle) to volume ratio as the support particles being employed.

Suitable supports are available from Saint-Gobain Norpro Co., Sud Chemie AG, Noritake Co., CeramTec AG, and Industrie Bitossi S.p.A. Without being limited to the specific compositions and formulations contained therein, further information on support compositions and methods for making supports may be found in U.S. Patent Publication No. 2007/0037991.

In order to produce a catalyst for the oxidation of an olefin to an olefin oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used.

A promoting amount of a rhenium component, which may be a rhenium-containing compound or a rhenium-containing complex, may also be deposited on the support, either prior to, coincidently with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount of alkali metal ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess silver impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

Epoxidation Process

The epoxidation process may be carried out by continuously contacting an oxygen-containing gas with an olefin, preferably ethylene, in the presence of the previously-described catalyst. Oxygen may be supplied to the reaction in substantially pure molecular form or in a mixture such as air. By way of example, typical reactant feed mixtures under operating conditions may contain from about 0.5% to about 45%, preferably about 5% to about 30% of ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum.

Also present in the reaction, as previously mentioned, are one or more chloride moderators non-limiting examples of which include organic halogen-containing compounds such as $C_1$ to $C_8$ halohydrocarbons; especially preferred are chloride-containing moderators such as methyl chloride, ethyl chloride, ethylene dichloride, vinyl chloride or mixtures thereof. Controlling chloride concentration level is particularly important with rhenium-containing catalysts.

A usual method for the ethylene epoxidation process comprises the vapor-phase oxidation of ethylene with molecular oxygen, in the presence of the previously described catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long filled with catalyst. Such reactors include a reactor outlet which allows the olefin oxide, un-used reactants, and byproducts to exit the reactor chamber.

In the present invention—the "post-conditioning" step is preceded by a "conditioning", "initiating" or "start-up" phase. In this start-up phase, the fresh catalyst is gradually heated over a period of about 10 hours to about 60 hours from an initial temperature in the range of 180° C. to about 220° C. to a conditioning temperature of about 240° C. to about 280° C., preferably about 245° C. to about 265° C. During this initial time period, the recycle loop to the ethylene oxide reactor is pressurized with a feed gas composition containing ethylene, oxygen and a suitable ballast gas such as methane or nitrogen (nitrogen is preferred). The oxygen and ethylene are initially present in small concentrations, such as about 1% to about 4% ethylene and about 0.3% to 0.5% oxygen. The feed composition may also contain one or more chlorides at a concentration of about 0.05 ppm to about 3 ppm, preferably about 0.5 ppm to about 1 ppm; the chlorides are added simultaneously with the hydrocarbon and oxygen. (All concentrations recited in this paragraph are by volume). During conditioning, the feed components, and in particular the chloride concentration may be varied according to operator's practical experience and well-known practice in the industry. During this start-up phase, it is possible to achieve selectivity performance comparable to the selectivity of the catalyst under normal initial operating conditions after the start-up process, so attention should be paid to maximizing EO production in order to provide the operator with additional economic efficiencies. Thus, as the temperature is increased, the levels of ethylene and oxygen in the feed are also increased to boost the production level of ethylene oxide so that ethylene oxide is produced at a level that is from 45% to 75% of the targeted full production level, as measured by $\Delta EO$ in the reactor effluent—meaning the $\Delta EO$ is greater than about 0.6%, preferably greater than about 1.5%. Accordingly during this stage of the start-up process, the feed gas composition will contain about 4% to about 20% of ethylene and about 3% to about 5% oxygen. Chloride levels are maintained at the same levels as in the previous step.

After reaching the conditioning temperature, the temperature is maintained or held for a time period of about 50 hours to about 150 hours—during which time the ethylene and oxygen concentration in the feed gas are further increased until ethylene oxide production levels comparable to full production levels are reached, during which the $\Delta EO$ is greater than about 2.0%, preferably greater than about 2.5%, more preferably in the range of 2.0%-4.0%, at this point when the ethylene and oxygen levels will be near or at final operating conditions and the ethylene oxide production levels comparable to full production levels the conditioning step is completed. (The above description of the conditioning or start-up process is only illustrative, the present invention is not specific to any particular conditioning or start-up process).

After the conditioning step, in the present invention the process continues with a post-conditioning step (the technical effect of which is explained above). In the post-conditioning step, the concentration of the chlorides in the reactor feed mixture is increased to about ppm to about 7 ppm making the catalyst significantly more active and thus, lowering the temperature to about 215° C. to about 225° C. over a period of about 10 hours to about 50 hours, and at the same time lowering the selectivity by as much as 4% to 5%. After reaching the temperature range and chloride concentration mentioned above, the catalyst is held at these conditions for a period of about 50 to about 150 hours. After the hold period, the chloride concentration in the reactor feed mixture is then decreased over a period of about 50 hours to 150 hours to a level that is comparable to conventional chloride operating levels for an epoxidation process—about 0.5 ppm to about 3 ppm. With this decrease in chloride concentration, selectivity quickly recovers—adding 4% to 5% of selectivity, while activity remains high—with the temperature rising outside of the conditioning range, but not significantly higher than about 230° C. to about 240° C. (Of course as the catalyst ages activity will gradually decrease as well). At this point the epoxidation reaction is then managed according to conventional practices for the duration of the catalyst's service life. The conditions for carrying out such an oxidation reaction in the presence of epoxidation catalysts broadly comprise those described throughout the present specification. This applies to feed mixtures, suitable temperatures, pressures, residence times, diluent materials, moderating agents, and recycle operations, or applying successive conversions in different reactors to increase the yields of ethylene oxide. The use of the present catalysts in ethylene oxidation reactions is in no way limited to the use of specific conditions among those which are known to be effective.

For purposes of illustration only, the following are conditions that are often used in current commercial ethylene oxide reactor units: a gas hourly space velocity (GHSV) of 1500-10,000 h$^{-1}$, a reactor inlet pressure of 150-400 psig, a coolant temperature of 180-315° C., an oxygen conversion level of 10-60%, and an EO production rate (work rate) of 7-20 lbs. EO/cu.ft. catalyst/hr and a change in ethylene oxide concentration, ΔEO, of from about 1.5% to about 4.5%. The feed composition in the reactor inlet after the completion of start-up and during normal operation typically comprises (by volume %) 1-40% ethylene, 3-12% $O_2$; 0.2% to 10%, preferably 0.2% to 6%, more preferably 0.2% to 5% of $CO_2$; 0-5% ethane, an amount of one or more chloride moderators, which are described herein; and the balance of the feed being comprised of argon, methane, nitrogen or mixtures thereof.

EXAMPLE

The invention will now be described in more detail with respect to the following non-limiting examples.

Two identical 6.5 gram rhenium-containing catalyst pellets were prepared and then crushed, ground and screened to provide a sample of 14-18 mesh particles. 6.5 grams of the material were then charged into two separate ¼" outer diameter heated microreactors with automated chloride control. The process in the first microreactor was operated according to the present invention while the process in the second microreactor was operated as a reference according to known techniques in the art. One catalyst sample (Catalyst Sample 1) was then conditioned and operated according to the prior art, while the other catalyst sample (Catalyst Sample 2) was conditioned and operated according to the present invention.

Both catalyst samples were first conditioned by heating the reactor to 245° C. for 100 hours with a feed concentration of about 1.1 ppm (by volume) ethyl chloride, 8% $C_2H_4$, 7% $O_2$, 2% $CO_2$, balance $N_2$, at a WHSV of 4760. The catalyst sample conditioned and operated according to the prior art (Catalyst Sample 1) was left under these conditions for 300 hours. The catalyst sample conditioned and operated according to the present invention (Catalyst Sample 2) was subjected to this conditioning regime for 100 hours and then subjected to post-conditioning.

At the beginning of this post-conditioning for Catalyst Sample 2 (operated according to the present invention) the chloride concentration in the reactor were increased to 5 ppm to achieve the lowest temperature possible while still maintaining a production rate of 3% to 3.1% ΔEO. As expected the reaction temperature fell to 220° C. and selectivity dipped as well, but to never less than 84%. It was found that in order to increase the chlorides further would require a reduction in the ΔEO. However, this was avoided in order to maximize process economics. The Catalyst Sample 2 was then held at this temperature for 100 hours while keeping the chloride concentration at 5 ppm. After being subjected to a chloride concentration of 5 ppm, the chloride concentration was then gradually reduced in steps from 5 ppm to 1 ppm while maintaining the temperature at around 220° C. and production rate in the range of 3% to 3.1% ΔEO. The time elapsed between when post-conditioning began and when 1 ppm chlorides concentration was reached was approximately 170 hours.

After the chloride concentration was gradually reduced to the 1 ppm level, the catalyst had lost some activity (i.e., the reaction temperature had increased) but selectivity had also improved considerably. Over a period of about 30 hours, the chloride concentration was increased to 2 ppm in order to prevent further loss of activity—at this point (at a combined total of condition and post-conditioning of 300 hours) the temperature was 230° C. and the selectivity was between 89% to 90%. After 300 hours, the Catalyst Sample 2 was then operated according to conventional operating procedures. The conditioning and post-conditioning scheme described in the immediate paragraphs can be summarized as follows:

|  |  | Catalyst Sample 1 | Catalyst Sample 2 |
|---|---|---|---|
| Conditioning |  | 1-300 hours | 1-100 hours |
| Post-Conditioning | (a) Increase [Chlorides] to 5 ppm; (b) hold at 5 ppm; (c) lower to 1 ppm |  | 100-270 hours |
|  | Increase [Chlorides] to 2 ppm |  | 270-300 Hours |

Figure 1:
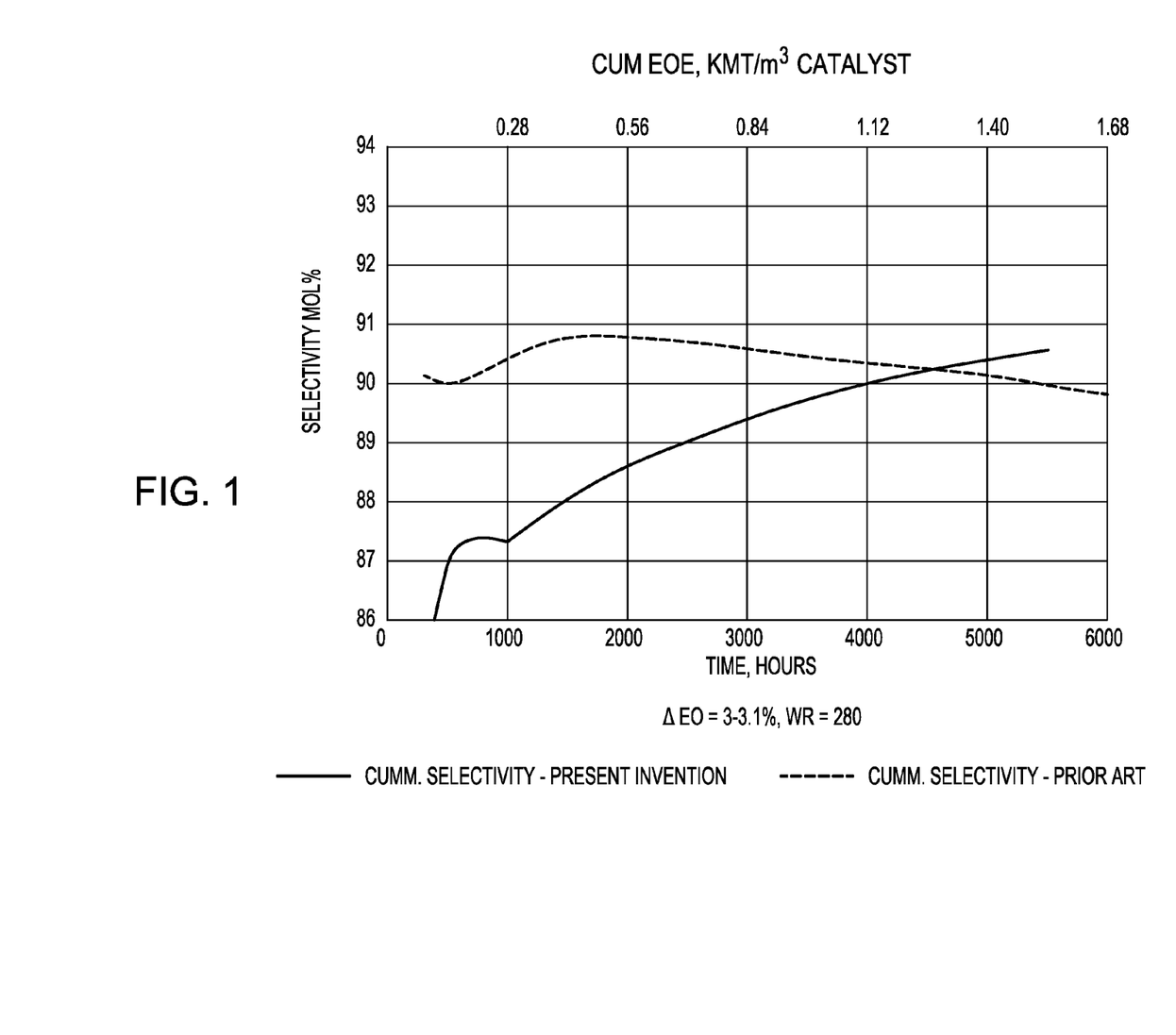
FIG. 1 is a graph for an ethylene oxide catalyst and process plotting the cumulative selectivity for operation according to the prior art and according to the present invention.
Figure 2:
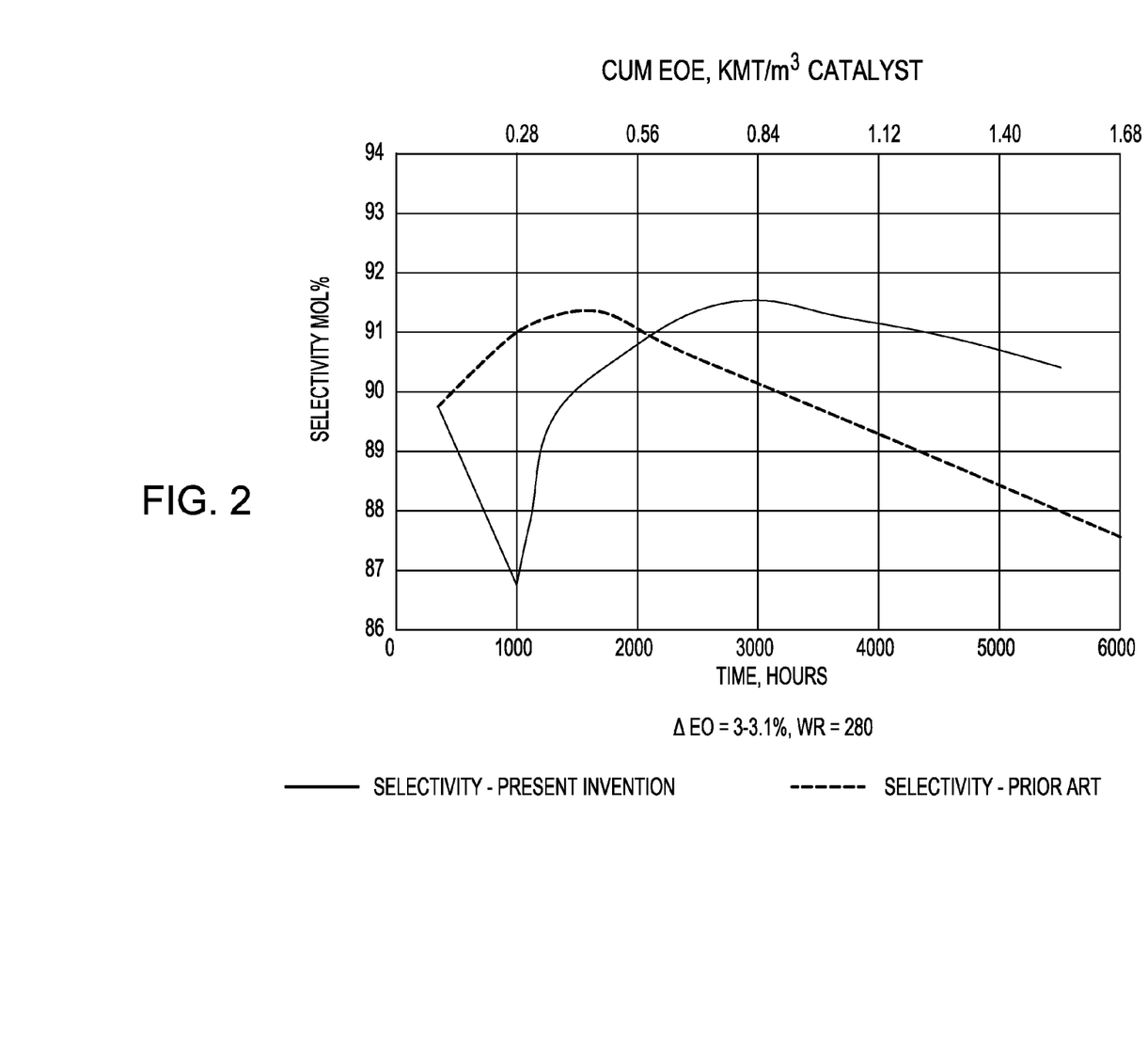
FIG. 2 is a graph for an ethylene oxide catalyst and process plotting instantaneous selectivity versus time for operation according to the prior art and according to the present invention.
Figure 3:
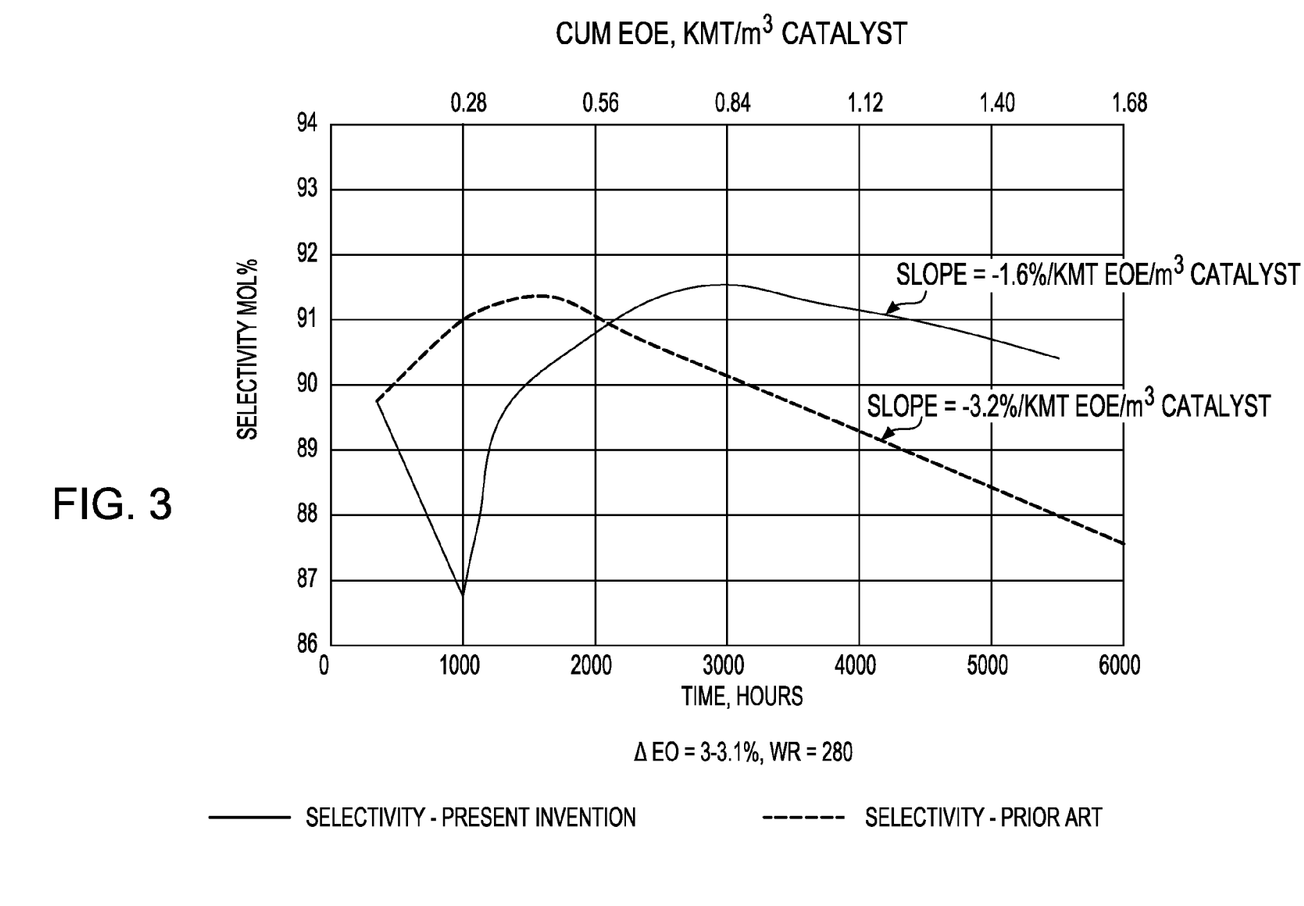
FIG. 3 is a graph for an ethylene oxide catalyst and process plotting the instantaneous selectivity for operation versus cumulative EOE production, according to the prior art and according to the present invention.

The selectivity performance measured from 300 hours onward was then measured and the results plotted in FIGS. 1-3. As can be seen in FIG. 2, in the epoxidation process practiced according to the present invention (Catalyst Sample 2) the instantaneous selectivity does fall significantly when the catalyst is exposed during the post-conditioning phase to high chloride concentrations—however, as described above, as soon as the chlorides are decreased to the normal chloride levels the instantaneous selectivity immediately increases and matches the instantaneous selectivity of the reference/prior art epoxidation process which did not include the high chloride post-conditioning step. In fact, the maximum instantaneous selectivity of the process practiced according to the present invention (91%) actually exceeds the maximum instantaneous selectivity of the reference process (90.5%). Thus, the process of the present invention leads to improved selectivity.

The benefits of the process according to the present invention can also be seen in terms of long-term stability. FIG. 1 shows the average cumulative selectivity—where each point on the curves represents the average selectivity for the run up until that point. By approximately 4500 hours, the process practiced according to the present invention has a higher average selectivity than the reference process because, as can be seen in FIG. 1 the catalyst in the process practiced according to the present invention is much more stable than the catalyst in the reference process.

This improved stability can also be seen in FIG. 3, where the curves of FIG. 2 are replotted as instantaneous selectivity versus cumulative EOE production. From the curves, a stability coefficient of the curves can be calculated—these coefficients are set forth in Table I, below. As can be seen, the catalyst in the process practiced according to the present invention is two-and-a-half times more stable than the catalyst in the reference process.

TABLE I

| Stability (in units of % Sel./KMT Cumulative EOE/m³ catalyst) | | |
| --- | --- | --- |
| Process | Catalyst Sample | Stability |
| Reference | 1 | −3.2 |
| Present Invention | 2 | −1.6 |

While the present invention has been particularly shown and described with respect to various embodiments thereof, it will be understood to those skilled in the art that the foregoing and other changes in forms and details may be made without departing from the spirit and scope of the present invention. It is therefore intended that the present invention not be limited to the exact forms and details described and illustrated, but fall within the scope of the appended claims.

We claim:

1. A method for the epoxidation of an olefin comprising:
   initiating an epoxidation reaction by reacting a feed gas composition containing ethylene, oxygen, and a chloride moderator present at a concentration of from about 0.5 ppm to about 3 ppm, in the presence of an epoxidation catalyst at a temperature of about 245° C. to about 265° C.;
   increasing the moderator concentration to about 5 ppm to about 7 ppm and lowering the temperature to about 215° C. to about 225° C.; and
   maintaining the moderator concentration within the range of 5 ppm to about 7 ppm and the temperature in the range of about 215° C. to about 225° C. for a time period of about 50 hours to about 150 hours.

2. The method according to claim 1, wherein subsequent to the maintaining step, the method further comprises the step of reducing the chloride concentration to between 0.5 ppm and 3 ppm and increasing the temperature to about 230° C. to about 240° C.

3. The method according to claim 1, wherein the chloride moderator is an organic halide.

4. The method according to claim 1, wherein the chloride moderator is selected from the group consisting of methyl chloride, ethyl chloride, ethylene dichloride and vinyl chloride.

5. The method according to claim 1, wherein the chloride moderator is selected from the group consisting of C1 to C8 halohydrocarbons.

6. The method of claim 1, where the feed gas composition contains about 1% to about 40% of ethylene, about 3% to about 12% oxygen, and about 0.2% to about 2% $CO_2$.

7. The method according to claim 1, wherein said epoxidation catalyst is a silver-based epoxidation catalyst that comprises a promoting amount of rhenium.

8. The method according to claim 7, wherein silver-based epoxidation catalyst further comprises a promoting amount of at least one alkali metal.

9. The method according to claim 1, wherein said increasing the moderator concentration to about 5 ppm to 7 ppm provides a 4% to 5% lowering of selectivity of said epoxidation catalyst.

10. A method for making an olefin glycol comprising the step of: (a) preparing olefin oxide according to the method of claim 1; and (b) reacting the olefin oxide with water to form an olefin glycol.

* * * * *